United States Patent [19]

Whelan

[11] 4,439,151
[45] Mar. 27, 1984

[54] DENTAL DEVICE

[76] Inventor: Cahal Whelan, Highview Rd., Pound Ridge, N.Y. 10576

[21] Appl. No.: 164,842

[22] Filed: Jun. 30, 1980

[51] Int. Cl.³ .................................... A61C 11/00
[52] U.S. Cl. .................................. 433/60; 433/74
[58] Field of Search ............................. 433/60, 74

[56] References Cited

U.S. PATENT DOCUMENTS 2,283,385  5/1942  Neustadt .................... 433/58
2,619,725 12/1952  Roeser ...................... 433/60

Primary Examiner—Robert Peshock
Attorney, Agent, or Firm—Spellman, Joel & Pelton

[57] ABSTRACT

A dental device is provided for fabricating dies from flexible impression material wherein the model, die and articulation mounting are accomplished in a single pouring. The device comprises a pair of recessed pivotal trays generally shaped to an individual's jaw. The member each includes inner and outer walls having internal ridges running vertically therealong at spaced distances and a base having predetermined spaced apertures thereabout to receive an insert. The trays are designed to be mounted face to face with a like member and open to 180°. The tray includes hollow cylindrical portions in the rear thereof, engaged by a transverse element for pivoting thereabout. A vertical stop pin is mounted through the distal arm to maintain the respective spacing of the trays. The insert member has downwardly projecting portions extending through the base apertures, a base engaging the base of the tray and an upwardly extending rib which is located centrally within the walls of the tray. The projecting portions of the plastic member may be pushed vertically to readily eject the mold from the articulator after it has hardened. The mold may be sectioned so that it is possible to remove and accurately replace sections individually.

8 Claims, 5 Drawing Figures

DENTAL DEVICE

BACKGROUND OF THE INVENTION

The present invention relates to a dental device for the manufacture of models and particularly a device having means to facilitate the removal and accurate replacement of all or part of the molded dies from the device.

Numerous methods and designs already exist for molding models i.e. making casts of the upper and lower dental arches to restore or replace teeth. The present invention provides a ready means of removing a molded model or portion thereof from a recessed tray. The device further provides a method of model fabrication and die location as well as articulation simultaneously within a single mechanism. Presently, there are problems with existing devices in removing the molds and working with the individual teeth. These drawbacks have been eliminated in the present invention where parallel ridges are included along the internal wall surfaces of the trays and an insert with projecting upper and lower ends is mounted within the trays. The element includes alternately spaced lower end portions which project through corresponding apertures in the base of the trays in order to facilitate removal of the molded model by pushing on the projected ends. The model can also be partitioned to permit working on single dies which can be accurately replaced in the original mold.

The prior art includes U.S. Pat. No. 4,103,424 to Benjamin et al, which describes the use of the transparent plastic material such as high impact polystyrene for the manufacture of disposable dental articulators. Other individual features or elements of the invention are shown in separate prior art applications such as U.S. Pat. No. 2,092,575 which illustrates the use of an adjustable stop pin for a dental articulator device and a retention or hinge pin for joining the upper and lower halves of the articulator. Finally, U.S. Pat. No. 3,495,33 to Kuhn discloses the use of retention ridges in a dental die former.

While the above patents appear to represent the most pertinent prior art without affecting the patentability of the invention, other patents of general interest do exist and may be pertinent to some degree such as U.S. Pat. No. 2,786,272 to Lindley; U.S. Pat. No. 3,577,640 to Lee; and U.S. Pat. No. 3,908,271 to Derda. Roeser U.S. Pat. No. 2,619,725 on a dental tray is also of interest as well as the additional Lindley U.S. Pat. No. 2,700,219.

SUMMARY OF THE INVENTION

The present invention relates to an improved dental device for the production of a working model.

The invention comprises a curved pivotal tray corresponding to an individual's jaw, which includes inner and outer walls and a base. The internal walls include parallel ridges spaced therealong and the base includes a plurality of alternating apertures extending therealong in a predetermined pattern. The tray is designed to be mounted face to face with a like member and be capable of pivoting or opening to 180°. The trays each have rearwardly extending portions terminating in circular portions having aligned apertures to receive a transverse pin for movement purposes including articulation and pouring of the tray impression. A curved member is centrally mounted within the trays by means of downwardly projecting portions which engage the apertures in the trays. The member also includes a vertically extending upper portion and a base which engages the base of the tray.

The device thus includes means to align two trays face to face in order to align an impression on one tray so that when the impression is poured the resulting model will fit into the opposite tray. The device also includes a means to pivot the trays apart to 180° to provide easy pouring of both tray and impressions into downward troughs. The device also includes a means to readily remove the poured model from the unit and to relocate the model back in the unit when desired. Furthermore, the device includes means to articulate said model with a counter-model of an extact replica unit and means to pour a model with removable dies and mount it on an articulator in one step. The insert member mounted in the base of the tray provides the means to remove the model or portions thereof by pushing on the lower projecting portions extending through the floor of the tray. The insert also provides a means to lock itself into the die material. In contrast, the usual method would involve setting up dowel pins in the impression, pouring in die stone sufficient to retain the dowel pins, pouring the base and articulating the models.

Accordingly, an object of this invention is to provide a new and improved dental device for producing models.

Another object of this invention is to provide a new and improved dental device for molding teeth, including means to readily remove and replace the entire mold or portions thereof from the die.

A more specific object of this invention is to provide a new and improved dental device for making models wherein the upper and lower castings are made within trays which include ridged, internal walls to facilitate mounting and dismounting of individual teeth and a central plastic member having projecting elements which extend through the base of the tray to facilitate removal by pushing on said projecting portions.

BRIEF DESCRIPTION OF THE DRAWINGS

Other objects and advantages of the present invention may be seen from the following description when viewed in conjunction with the accompanying drawings wherein.

DETAILED DESCRIPTION OF THE INVENTION

Figure 1:
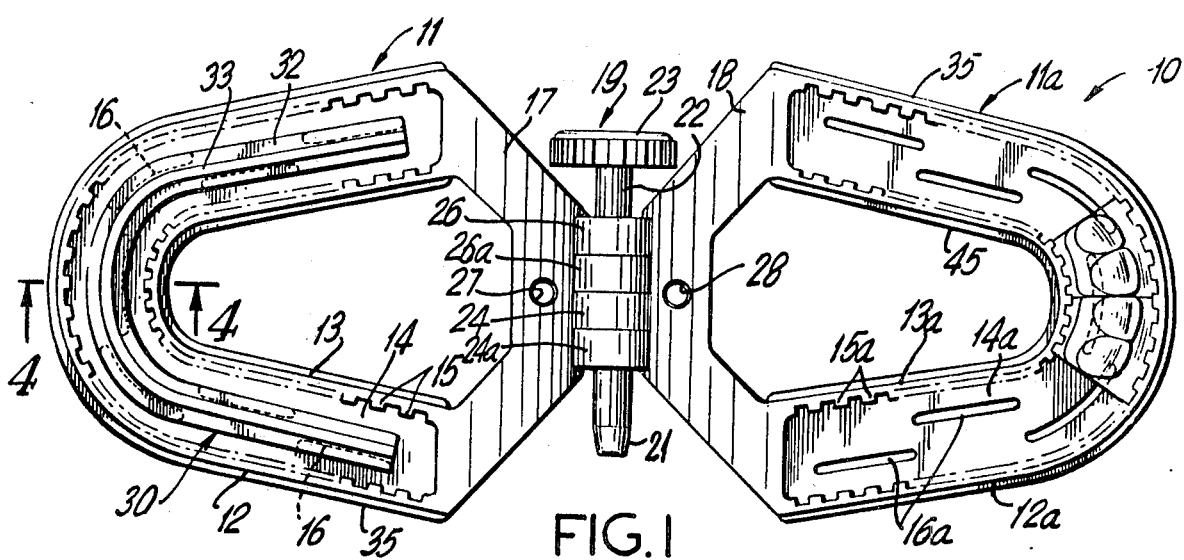
FIG. 1 is a top view of the dental device comprising the invention.
Figure 2:
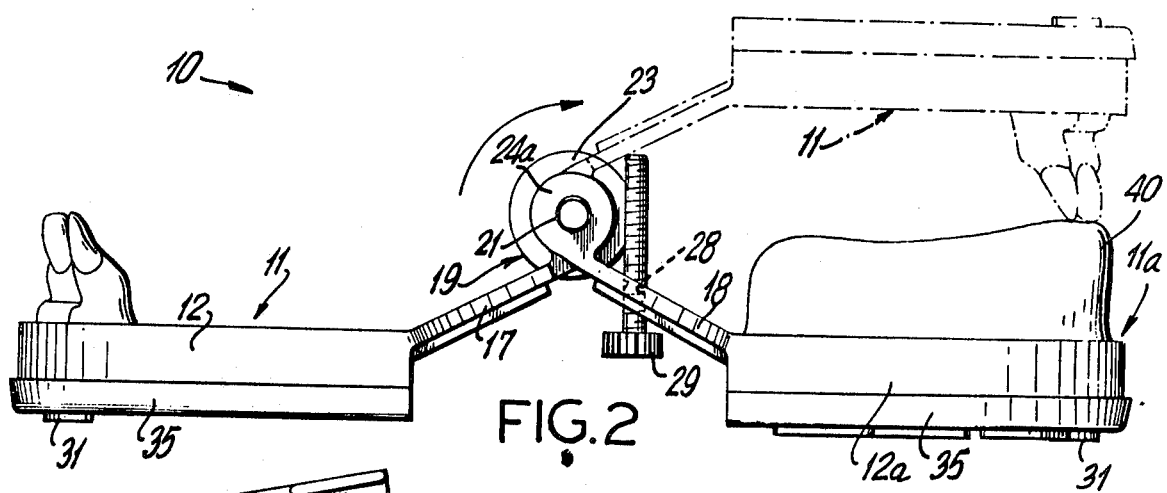
FIG. 2 is a side view of the invention.
Figure 3:
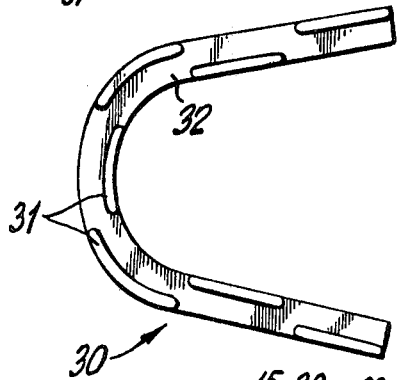
FIG. 3 is a view of the insert utilized in conjunction with the subject dental device.
Figure 4:
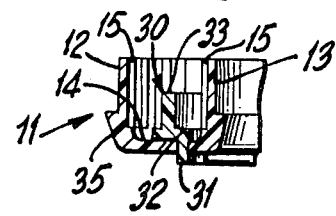
FIG. 4 is a view taken along the lines 4—4 of FIG. 1.
Figure 5:
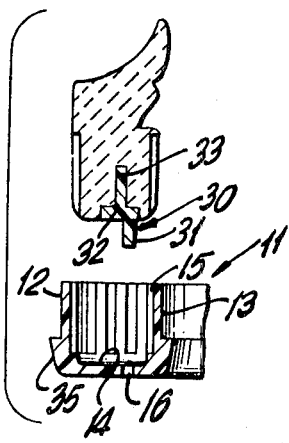
FIG. 5 is an exploded cross-sectional view of FIG. 4.

Referring now to the drawings, the invention comprises a dental device 10 which includes reuseable upper and lower curved pivotal trays 11 and 11a corresponding to an individual's jaw. The trays 11 and 11a are identical so that a tray could be used for the upper or lower portion of a mold. Each tray 11, 11a, includes a recessed portion formed, respectively, by inner and outer walls, 12 and 12a, 13 and 13a, and a base 14, 14a. The internal walls 12, 12a, 13, 13a, include tapered parallel ridges 15, 15a, therealong and the bases 14 and 14a each include a plurality of spaced alternating apertures 16 and 16a extending therealong in a predetermined pattern. The pattern comprises an initial pair of alternating spaced apertures or slots at each end of the trays, 11, 11a, which run in substantially parallel planes to one another, a pair of curved apertures spaced from the closer end aperture and a curved aperture towards the rear of the base 14, 14a, at the front portion of the tray.

The trays, 11, 11a, each include rearwardly projecting portions 17 and 18 which project inwardly at an angle from the rear of the recessed portion and terminate in a pair of hollow, cylindrical members 24 and 26. In an alternate embodiment, the cylindrical members of each pair 24, 26 and 24a, 26a, could be mounted on separate arms extending back from the respective trays 11, 11a. The hollow, cylindrical members 24 and 26 on the tray 11 are offset at the rear surface 25 so that the correspondingly offset members 24a and 26a may mesh together. One of said cylinders 26a would be located between 24 and 26 while the other 24a would be on the outside of the offset cylinder 24. An elongated adjusting member 19, a tapered end 21 having a body portion 22 and a knob 23 at the other end is designed to fixedly engage cylinder members 24 and 26, 24a and 26a.

The rear portion 17, 18 of the trays 11, 11a, include corresponding threaded apertures 27, 28 which are designed to receive a stop pin 29 to maintain the trays 11, 11a, in a predetermined relationship for articulation purposes. The device 10 also includes a pair of curved internal members 30 having alternating downwardly projecting portions 31 which engage and extend through the apertures 16, 16a, in the trays, a base portion 32 which engages the base 14, 14a, of the trays 11, 11a, and an upwardly extending portion 33 which becomes part of the model. The downwardly extending portions 31 may be pushed upwardly to readily eject the mold or a portion thereof from the trays 11, 11a.

The device 10, as thus described above, includes means to align an impression on one tray 11 so that when the impression is poured the resulting model 40 will fit into the opposite tray 11a. The member 30 provides a locating system wherein the poured model 40 may be readily removed from a tray 11, 11a, by pushing on the portions 31 extending through the base 14, 14a, and relocated back even after sectioning by fitting the protruding portions 31 into the apertures 16, 16a. The molded section is keyed to fit a particular aperture 16, 16a, and is slid therein with an assist from the retention ridges 15. The device 10 includes a protruding buccal ridge 35 extending peripherially about the outer surface of each tray to facilitate removal from the molds and a liquid 45 extending circumferentially about the inner surface of each tray.

In essence, the device 10 provides a practical means to pour a model with removable dies and mount it on an articulator in one step rather than the conventional method which involves setting dowel pins in the impression, pouring the stone sufficient to retain the dowel pins, pouring the base and articulating the models 40. Here, a device 10 is provided to pour a model 40 and mounted on an articulator in one step. The single axis hinge formed by the cylinders 24, 26, and elongated member 19 involves a minimal inclination of the struts so that their inclination and length are an accurate approximation of the typical width of the candidate model and its counter in combination. The integral design of device 10 provides sufficient strength while permitting lightweight fabrication.

It is understood that the above-described arrangements are merely illustrative examples of the application. Numerous other arrangements may be readily devised by those skilled in the art which will embody the principles of the invention and fall within the spirit and scope thereof.

I claim:

1. A dental device for fabricating models comprising:
   a recessed tray having a base and inner and outer walls extending upwardly therefrom, said base having apertures extending therethrough in a predetermined pattern and a rear portion extending upwardly from the tray and having a pair of spaced, hollow cylindrical members at the end thereof, and
   a member mounted within the tray, having predetermined lower portions extending through the apertures in the base of the tray, a base, and an upwardly extending portion integrally engageable by the model which is formed within the tray wherein the model may be readily ejected from the tray by pressing on the lower projecting portions thereof.

2. A dental device in accordance with claim 1:
   the inner and outer walls of the tray comprise a plurality of ridges which extend upwardly from the base to permit accurate relocation of the model in the tray and wherein said ridges are parallel to adjacent ridges on the same wall but not to ridges on the opposite wall to prevent accidental dislocation of separated sections.

3. A dental device in accordance with claim 2 wherein:
   the inner and outer walls are tapered to retain the model therein.

4. A dental device in accordance with claim 2 further including:
   a second tray identical to the first tray and a member mounted within said tray identical to the member mounted within the first tray, and
   a pin member adapted to engage the apertures in the hollow cylindrical members to join the first and second identical trays for pivoting movement.

5. A dental device in accordance with claim 4 further includes:
   an adjustable stop member mounted in one of said trays and extending towards the other tray to maintain a spaced distance between said trays.

6. A dental device in accordance with claim 4 further including:
   a separate protruding ridge extending circumferentially about the outer and inner surface of each tray to facilitate removal of the model.

7. A dental device in accordance with claim 4 further including:
   a single axis hinge on the rear end of each tray with struts having a minimal inclination mounted thereto such that the inclination and length are an accurate approximation of the mold and its counter.

8. A dental device in accordance with claim 4 wherein:
   the dental device acts as a jig to locate an impression which when poured will yield a model and wherein the pin member comprises an elongated body engaging the interlocking hollow cylinders and a knob for gripping purposes such that the trays can be pivoted 180° apart for pouring of the model mold.

* * * * *